(12) United States Patent
Chan et al.

(10) Patent No.: US 7,736,849 B2
(45) Date of Patent: Jun. 15, 2010

(54) OLIGONUCLEOTIDES TARGETING THE UL73 GENE REGION AND USE THEREOF

(75) Inventors: Yu-Jiun Chan, Taipei (TW); Jui-Chu Lin, Taipei (TW); Cheng-Yi Liu, Taipei (TW); Ming-Tak Ho, Taipei (TW)

(73) Assignee: Taipei Veterans General Hospital, VAC, Taipei (TW)

( * ) Notice: Subject to any disclaimer, the term of this patent is extended or adjusted under 35 U.S.C. 154(b) by 326 days.

(21) Appl. No.: 11/459,329

(22) Filed: Jul. 21, 2006

(65) Prior Publication Data

US 2008/0032280 A1    Feb. 7, 2008

(51) Int. Cl.
 *C12Q 1/70*  (2006.01)
 *C12P 19/34*  (2006.01)
(52) U.S. Cl. .......................................... 435/5; 435/91.2
(58) Field of Classification Search ............... 435/5, 435/91.2; 536/24.3
 See application file for complete search history.

(56) References Cited

U.S. PATENT DOCUMENTS

| 5,853,981 | A | 12/1998 | Kondo et al. | |
|---|---|---|---|---|
| 2002/0102536 | A1* | 8/2002 | Boursnell | 435/5 |
| 2004/0228842 | A1* | 11/2004 | Lu et al. | 424/93.2 |

OTHER PUBLICATIONS

Buck et al., BioTechniques 27, 528-536 (1999).*
Database Accession No. CN378881/c (May 2005).*
Database Accession No. CO119542/c (2004).*
Database Accession No. AI936692 (2000).*
Lowe et al., Nucleic Acids Research 18(7), 1757-1761 (1990).*
S. Pignatelli et al., Immunoelectron Microscopy Analysis of HCMV gpUL73 (gN) Localization, Archives of Virology 2002, 147: 1247-1256.
S. Pignatelli et al., Human Cytomegalovirus Glycoprotein N (gpUL73-gN) Genomic Variants: Identification of a Novel Subgroup, Geographical Distribution and Evidence of Positive Selective Pressure, Journal of General Virology (2003) 84, 647-655.
J. Sambrook, E.F. Friitsch, and T. Maniatis; Molecular Cloning, Protocols for cDNA Cloning, 853-8.81, A Laboratory Manual (Cold Spring Harbor Laboratory Press, Second Edition, New York, 1989).
Hsin-Pai Chen et al., The type-2 variant of human cytomegalovirus glycoprotein N (gN-2) is not the rarest in the Chinese population of Taiwan: Influence of primer design, Journal of Virological Methods, 151 (2008) 161-164.

* cited by examiner

*Primary Examiner*—Kenneth R. Horlick
(74) *Attorney, Agent, or Firm*—WPAT, P.C.; Anthony King (57) ABSTRACT

The present invention provides an oligonucleotide for amplifying a nucleic acid of human cytomegalovirus and a kit for detecting human cytomegalovirus. The present invention also provides an oligonucleotide for identifying a nucleic acid of human cytomegalovirus. The present invention further provides a method of detecting human cytomegalovirus in an individual.

1 Claim, 5 Drawing Sheets

OLIGONUCLEOTIDES TARGETING THE UL73 GENE REGION AND USE THEREOF

FIELD OF THE INVENTION

The present invention provides a method for detecting human cytomegalovirus. The present invention further provides a kit for detecting human cytomegalovirus.

BACKGROUND OF THE INVENTION

Human cytomegalovirus (CMV) is a ubiquitous agent in human populations. Infections are generally asymptomatic, but there can be serious medical sequelae in immunocompromised individuals and in congenitally infected newborns. In immunocompromised individuals, CMV infection can result in interstitial pneumonia, retinitis progressing to blindness and disseminated infection. Infections in newborns can be severely damaging, with multiple organ involvement including the central nervous system and may also result in auditory damage. The mechanisms of pathogenesis are not understood, although it is believed that host factors, such as cellular and/or humoral immune responses might be involved.

CMV infects between 50-100% of all individuals worldwide depending on age and socioeconomic status. CMV is naturally transmitted via saliva, urine or breast milk but can also be recovered from other body secretions. In addition, CMV can be transmitted transplacentally to the fetus, by geno-urinary contact during birth or intercourse, by blood transfusion (especially white cells) and bone marrow or organ transplant.

CMV is associated with a wide variety of disease syndromes both in the immunocompetent and in the immunocompromised host, although the latter are much more frequent and associated with significantly greater morbidity and mortality. Primary infection in the immunocompetent host usually goes unnoticed. However CMV is considered to be causing 10% of the mononucleosis syndrome in adolescents and young adults and is frequently associated with acute nonA-G hepatitis. Primary infection in pregnant women is associated with the transplacental transfer of CMV to the fetus.

CMV is a significant opportunistic pathogen responsible for serious clinical consequences in a variety of immunosuppressed patient groups such as neonate and infants, persons with AIDS and individuals undergoing immunosuppressive regimes for the purpose of organ or bone marrow transplantation. As is true for other human herpes viruses, CMV establishes a life-long latent infection with its human host and is ubiquitous in the population with high infectivity rate found in the United States.

Although latent infection by CMV is widespread and reactivation of latent virus after either immunosuppression or progressive immunodeficiency is the single most important contributor to emergence of CMV disease, the site(s) of viral latency remain poorly characterized.

CMV-specific diagnosis can be achieved by a variety of techniques directly detecting viral components or indirectly measuring changes in the host immune status. Reliable diagnostic approaches require sensitive and reproducible technology based upon well defined and highly CMV-specific reagents and a detailed understanding of the molecular processes underlying CMV-infection in the human host.

An UL73-encoded structural glycoprotein (gN) expressed on the cell surface of infected cells (S. Pignatelli, et al., Arch Virol. 2002, 147:1247-56). The protein is highly polymorphic in the N-terminus, but conserved in the C-terminus (S. Pignatelli, et al. J Gen Virol. 2003, 84:647-5).

BRIEF DESCRIPTION OF THE DRAWINGS

FIG. 1 (a) shows the figure of UL73/74 (including UL73-C1 and UL73-C2) gene sequence of CMV and the position of primers and probes of the present invention and (b) illustrates the plasmid map used in the present invention.

FIG. 4 (a) shows linearity relationship illustrating PCR result of different DNA samples concentration which the primer pair of the present invention (SEQ ID NOs: 3 and 4) and (b) shows linearity relationship illustrating PCR result of different DNA samples concentration by commercial CMM kit.

In FIG. 6, "—" means the linearity of the present invention and "---" means the linearity of commercial CMM kit.

DESCRIPTION OF THE INVENTION

Detection of CMV infection at a primary or reactive stage is important for performing effective preemptive antiviral treatment. Currently, the detection of primary or reactivated CMV infection is made by positive CMV cultures, positive antigenemia assay, or positive molecular assays. However, the current assays have drawbacks such as laborious, variability, false negative, time consuming etc., and cannot timely and effectively find CMV infection. The present invention improves the above disadvantages and provides oligonucleotides and methods for amplifying and detecting CMV and kits comprising these oligonucleotides.

Accordingly, the present invention provides, a primer, i.e., an oligonucleotide for amplifying a nucleic acid of human cytomegalovirus, the oligonucleotide comprising (i) a nucleic acid sequence consisting of at least fifteen continuous bases selected from the nucleic acid sequence of SEQ ID No: 13, SEQ ID No: 14, SEQ ID No: 15, SEQ ID No: 16, SEQ ID No: 17, SEQ ID No: 18 and SEQ ID No: 22, and (ii) a nucleic acid sequence fully complementary to the nucleic acid sequence of (i).

In preferred embodiments, the primer of the present invention comprises at least 16, 17, 18, 19, 20, 21, 22, 23, 24, 25, 26, 27, 28, 29 or 30 continuous bases of the full-length sequence set forth in SEQ ID No: 13, SEQ ID No: 14, SEQ ID No: 15, SEQ ID No: 16, SEQ ID No: 17, SEQ ID No: 18 or SEQ ID No: 22, or its fully complementary nucleic acid thereof.

In a more preferred embodiment, the primer of the present invention comprises (iii) a nucleic acid sequence consisting of at least fifteen continuous bases selected from the nucleic acid sequence of SEQ ID No: 1, SEQ ID No: 2, SEQ ID No:

3, SEQ ID No: 4, SEQ ID No: 5, SEQ ID No: 6 and SEQ ID No: 12, and (iv) a nucleic acid sequence fully complementary to the nucleic acid sequence of (iii).

In a further preferred embodiment, the primer of the present invention comprises (v) a nucleic acid sequence selected from the nucleic acid sequence of SEQ ID No: 1, SEQ ID No: 2, SEQ ID No: 3, SEQ ID No: 4, SEQ ID No: 5, SEQ ID No: 6 and SEQ ID No: 12, and (vi) a nucleic acid sequence fully complementary to the nucleic acid sequence of (v).

The term "nucleic acid" as used herein, refer to a deoxyribonucleotide or ribonucleotide polymer in either single- or double-stranded form, and unless otherwise limited, would encompass analogs of natural nucleotide that can function in a similar manner as naturally occurring nucleotide. Nucleic acids may be cloned or synthesized using any technique known in the art.

The term "complementary" as used herein, refer to the natural binding of nucleotides under permissive salt and temperature conditions by base-pairing. For example, the sequence "A-G-T" binds to the complementary sequence "T-C-A." Complementarity between two single-stranded molecules may be "partial", in which only some of the nucleic acids bind, or it may be complete when total complementarity exists between the single stranded molecules. The degree of complementarity between nucleic acid strands has significant effects on the efficiency and strength of hybridization between nucleic acid strands.

The term "mRNA" as used herein, refers to transcripts of a gene. Transcripts are RNA including, for example, mature messenger RNA ready for translation, products of various stages of transcript processing. Transcript processing may include splicing, editing and degradation. During gene transcription, introns, like exons, are transcribed into RNA but are subsequently removed by RNA splicing.

Figure 1:
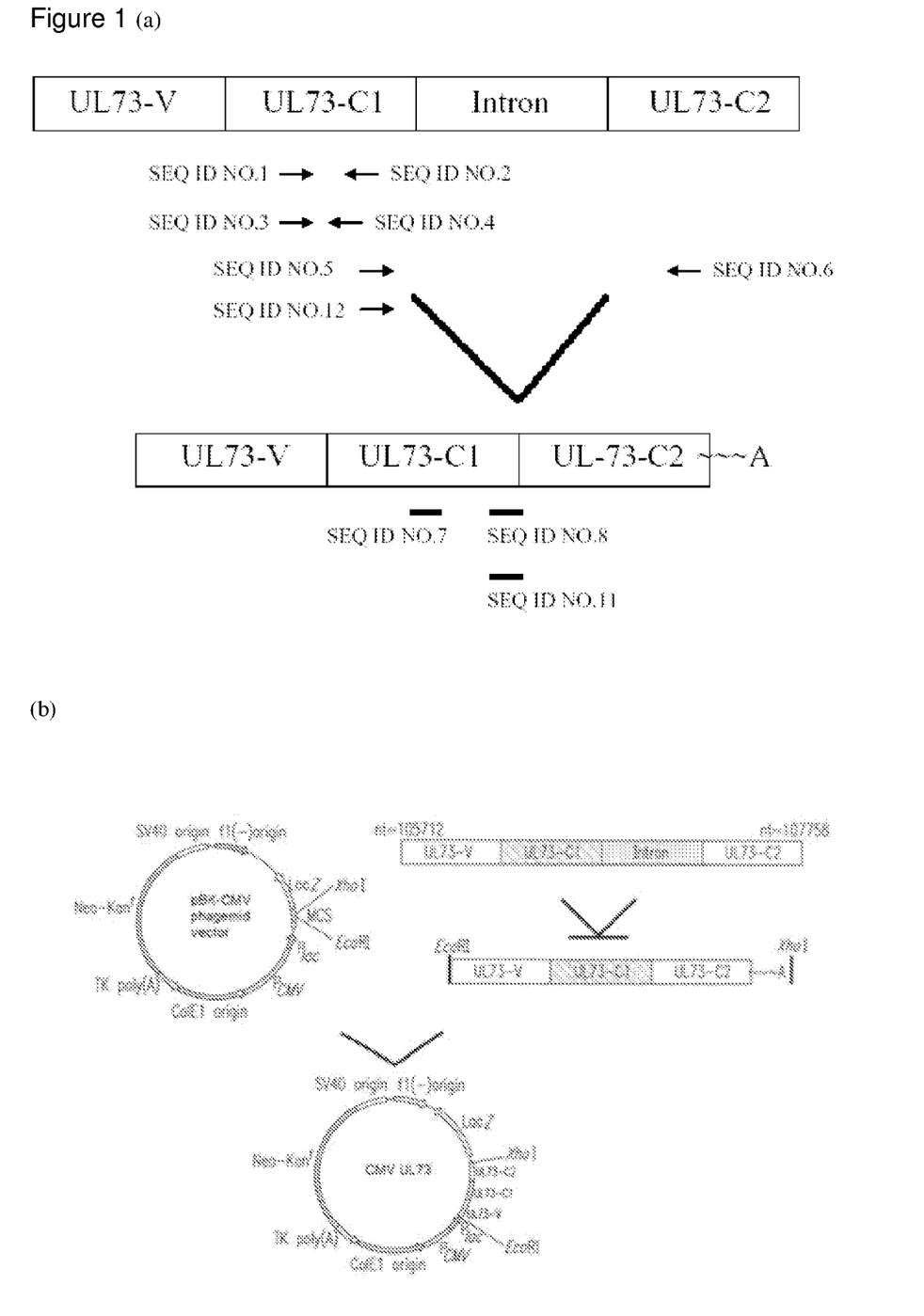

The term "UL73/74" as used herein, refers to gene region of CMV UL73 including UL73-C1 and UL73-C2 illustrated as FIG. 1. In fact, UL73-C2 involves part of currently named UL74 but the main function of UL73-C2 is related to UL73. To avoid making mistake, UL73/74 used herein represents UL73 including UL73-C1 and UL73-C2.

To effectively identify human cytomegalovirus, the present invention also provides a probe, i.e., an oligonucleotide for identifying a nucleic acid of human cytomegalovirus, the oligonueclotide comprising (a) a nucleic acid sequence consisting of at least ten continuous bases selected from the nucleic acid sequence of SEQ ID No: 19, SEQ ID No: 20 and SEQ ID No: 21, and (b) a nucleic acid sequence fully complementary to the nucleic acid sequence of (a).

In preferred embodiments, the probe of the present invention comprises at least 11, 12, 13, 14, 15, 16, 17, 18, 19 or 20 continuous bases of the full-length sequence set forth in SEQ ID No: 19, SEQ ID No: 20 or SEQ ID No: 21, or its fully complementary nucleic acid thereof. Various low or high stringency hybridization conditions may be used depending upon the specificity and selectivity desired.

In a more preferred embodiment, the probe of the present invention comprises (c) a nucleic acid sequence consisting of at least ten continuous bases selected from the nucleic acid sequence of SEQ ID No: 7, SEQ ID No: 8 and SEQ ID No: 11, and (d) a nucleic acid sequence fully complementary to the nucleic acid sequence of (c).

In a further preferred embodiment, the probe of the present invention comprises (e) a nucleic acid sequence selected from the nucleic acid sequence of SEQ ID No: 7, SEQ ID No: 8 and SEQ ID No: 11, and (f) a nucleic acid sequence fully complementary to the nucleic acid sequence of (e).

To facilitate ready use for CMV detection, the present invention further provides a kit for detecting human cytomegalovirus comprising the oligonucleotide of the present invention for amplifying a nucleic acid of human cytomegalovirus. In a preferred embodiment, the kit comprises an oligonucleotide comprising (iii) a nucleic acid sequence consisting of at least fifteen continuous bases selected from the nucleic acid sequence of SEQ ID No: 1, SEQ ID No: 2, SEQ ID No: 3, SEQ ID No: 4, SEQ ID No: 5, SEQ ID No: 6 and SEQ ID No: 12, and (iv) a nucleic acid sequence fully complementary to the nucleic acid sequence of (iii). In a more preferred embodiment, the kit comprises an oligonucleotide comprising (v) a nucleic acid sequence selected from the nucleic acid sequence of SEQ ID No: 1, SEQ ID No: 2, SEQ ID No: 3, SEQ ID No: 4, SEQ ID No: 5, SEQ ID No: 6 and SEQ ID No: 12, and (vi) a nucleic acid sequence fully complementary to the nucleic acid sequence of (v).

In addition to the primer of the present invention, the kit of the present invention further comprises the probe of the present invention.

The present invention further provides a method of detecting human cytomegalovirus in an individual comprising:

(a) isolating a nucleic acid from a sample from the individual;

(b) providing an amplification reagent and a primer pair selected from the group consisting of the oligonucleotide of the present invention, wherein the primer pair is (i) SEQ ID NOs: 13 and 14; (ii) SEQ ID NOs: 15 and 16; (iii) SEQ ID NOs: 17 and 18; or (iv) SEQ ID NOs: 22 and 18;

(c) amplifying a target fragment corresponding to said primer pair; and (d) identifying the amplified fragment by gel electrophoresis followed by staining with ethidium bromide or by the oligonucleotide of the present invention as a probe.

The term "sample", as used herein, is used in its broadest sense. A biological sample suspected of containing nucleic acid encoding human cytomegalovirus, or fragments thereof may comprise a bodily fluid, extract from a cell, chromosome, organelle, or membrane isolated from a cell, a cell, genomic DNA, RNA, or cDNA (in solution or bound to a solid support, a tissue, a tissue print, and the like).

In the method of the present invention, the amplification is made by polymerase chain reaction (PCR). The preferred embodiment of PCR is real-time PCR.

The method of the present invention can effectively find latency or activation of CMV. Accordingly, the method of the present invention identifies the latent of cytomegalovirus based on the presence of the corresponding fragment from primer pair of SEQ ID NOs: 13 and 14 and/or SEQ ID NOs: 15 and 16 but the absence of the corresponding fragment from primer pair of SEQ ID NOs: 17 and 18 and/or SEQ ID NOs: 22 and 18. To make confirmation, if the fragment is hybridized with SEQ ID NO: 19 but without SEQ ID NO: 20 or SEQ ID NO: 21, the test result further identify CMV latency inside a patient. In a preferred embodiment, the probes are oligonucleotides of SEQ ID NO: 7, SEQ ID NO: 8 and SEQ ID NO: 11.

In addition, the method of the present invention identifies the activation of cytomegalovirus based on the presence of the corresponding fragment from primer pair of SEQ ID NOs: 13 and 14 and/or SEQ ID NOs: 15 and 16 together with the presence of the corresponding fragment from primer pair of SEQ ID NOs: 17 and 18 and/or SEQ ID NOs: 22 and 18. To make confirmation, if the fragment is hybridized with SEQ ID NO: 19 and SEQ ID NO: 20 or SEQ ID NO: 21, the test result further identify CMV activation inside a patient. In a preferred embodiment, the probes are oligonucleotides of SEQ ID NO: 7, SEQ ID NO: 8 and SEQ ID NO: 11.

The term "hybridization", as used herein, refers to any process by which a strand of nucleic acid binds with a complementary strand through base pairing to form a hybridization complex between two nucleic acid sequences by virtue of the formation of hydrogen bonds between complementary G and C bases and between complementary A and T bases. These hydrogen bonds may be further stabilized by base stacking interactions. The two complementary nucleic acid sequences hydrogen bond in an antiparallel configuration. A hybridization complex may be formed in solution or between one nucleic acid sequence present in solution and another nucleic acid sequence immobilized on a solid support (e.g., paper, membranes, filters, chips, pins or glass slides, or any other appropriate substrate to which cells or their nucleic acids have been fixed). The amplification reagent used in the present invention includes but is not limited to dNTP and DNA polymerase.

The probe of the the present invention can link a label. A wide variety of labels and conjugation techniques are known by those skilled in the art and may be used in various nucleic acid and amino acid assays. Means for producing labeled hybridization or PCR probes for detecting sequences related to polynucleotides include oligolabeling, nick translation, end-labeling or PCR amplification using a labeled nucleotide. Suitable labels, which may be used for ease of detection, include radionuclides, enzymes, fluorescent, chemiluminescent, or chromogenic agents as well as substrates, cofactors, inhibitors, magnetic particles, and the like.

The examples below are non-limiting and are merely representative of various aspects and features of the present invention.

EXAMPLE

Example 1

Preparation of sample and control

Plasmid of CMV UL73 illustrated as FIG. 1(b) was prepared as cloning vectors by general technique for making cDNA cloning such as J. Sambrook, E. F Fritsch, and T.Maniatis in *Molecular Cloning, A Laboratory Manual* (Cold Spring Harbor Laboratory Press, Second Edition, New York, 1989).

In order to identify the primers and probes of the present invention specific to UL73/74, herpes simplex was tested as a negative control in all examples.

Extraction of CMV DNA from Samples:

216 various CMV samples including 2 CSF samples, 6 urine samples, 10 BAL samples, 44 serum samples, 148 whole blood samples, 6 other specimens were collected. DNA from these samples were extracted and purified by QIAGEN DNA blood mini kit, The purified DNA were dissolved in 200 µl of elution buffer and stored at −80° C. in a refrigerator.

CMV Late gene PCR:

CMV late gene involved in general assay was used as a control group in PCR reaction.

Figure 2:
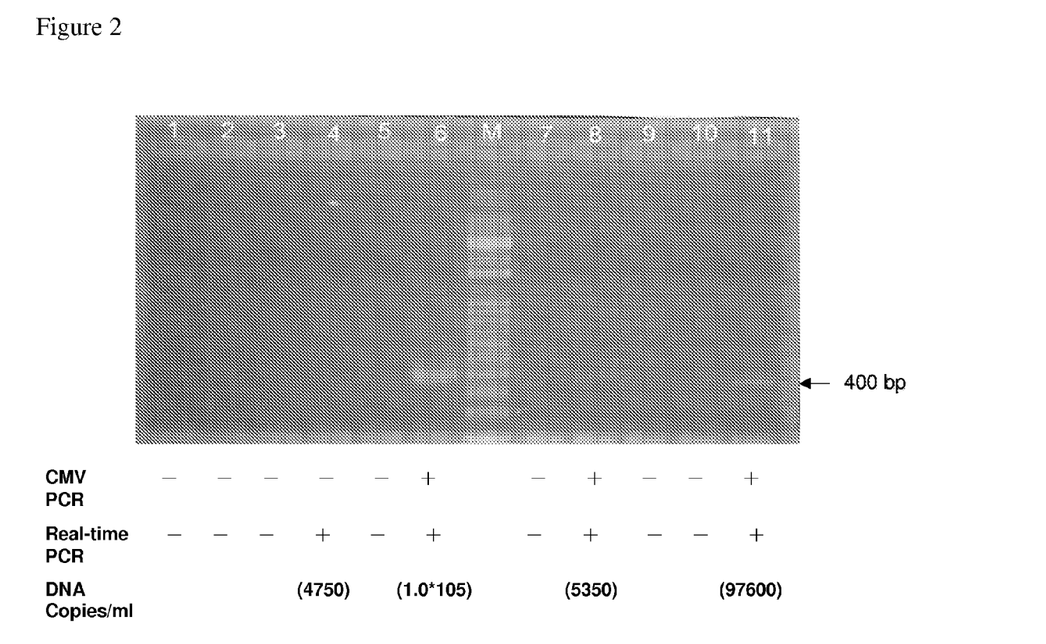
FIG. 2 shows the electrophoresis illustration of PCR product that indicates the sensitivity of CMV late gene primer compared with the primer of the present invention. In the figure, M means marker.

5 µl extracted CMV DNA were added into PCR solution to make 50 µl of total volume. The primer pair of late gene was SEQ ID NO: 9, 5'-cacctgtcaccgctgctatatttgc-3' and SEQ ID NO: 10, 5'-caccacgcagcggcccttgatgttt-3'. The DNA were amplified by the use of Perkimer Elmer thermal cycler. The total reaction for PCR required 40 cycles under the condition as follows: 94° C. for 2 minutes, 65° C. for 1.5 minutes, 72° C. for 1 minutes, and additional 10 seconds at each cycle. Final extension was set at 72° C. for 10 minutes to complete the amplification process. The size of product around 400 bps was identified by electrophoresis. As showed in FIG. 2, the electrophoresis illustration of PCR product indicates the sensitivity of CMV late gene primer compared with the primer of the present invention. Lanes 1-5 and 8-11 were related to the test results based on blood or serum samples Lanes 6 and 7 showed positive and negative control groups, separately. Lane M was 100 base pair marker. As the result of the clinical samples test, the primer pair of the present invention (SEQ ID NOs: 3 and 4) still could detect CMV DNA under the lower concentration.

Example 2

Real-Time PCR Proceeded with the Primer Pair of the Present Invention (A) 3 µl DNA samples (clinical samples and control) and 200 µm primer pair mixture which consisted of SEQ ID NO: 1, 5'-atcgcatatg tatgagctctcactgtc-3' and SEQ ID NO: 2, 5'-tctggaagcagcaatgtcgtagtac-3' were added into 12.5 µl SYBR Master Mix reaction solution (SYBR Green I PCR Master Mix, Applied Biosystems) to make 25 µl of total volume for PCR reaction. The reaction was heated at 50° C. for 2 minutes at first. Then, 45 cycles was performed. Each cycle included denaturation (95° C. for 15 seconds), annealing-extension (60° C. for 60 seconds) and dissociation (60-95° C.).

Figure 3:
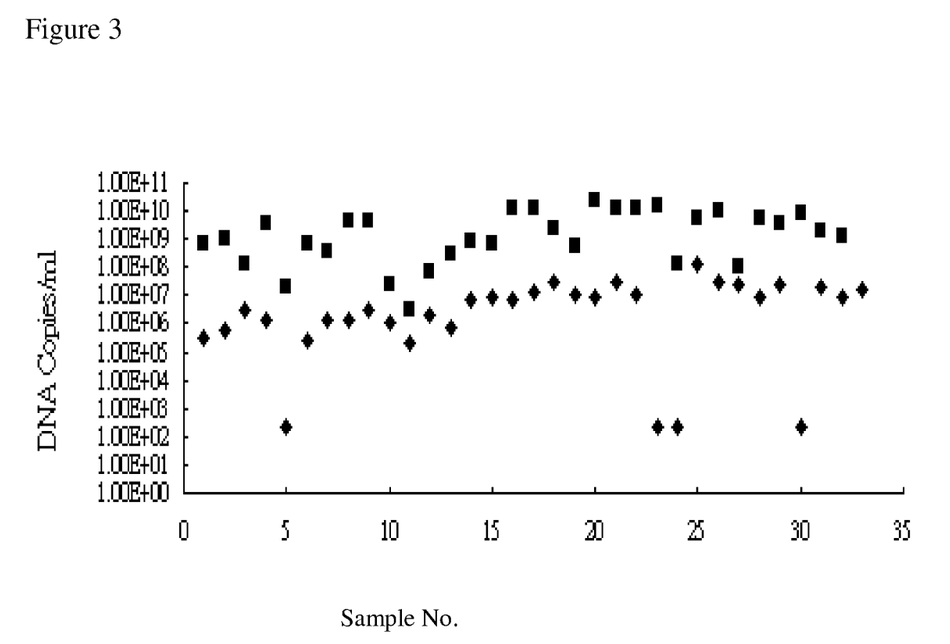
FIG. 3 shows the result of the sensitivity of the primer pair of the present invention. In the figure, ♦ means commercial CMM kit and ■ means the test kit of the present invention.

33 CMV viral isolates and 4 herpes simplex negative controls were tested by primer SEQ ID NOs: 1 and 2, and commercial Roche CMM kit, respectively. As depicted in FIG. 3, the primer SEQ ID NOs: 1 and 2 could detect DNA molecular from 100 to $10^9$ copies/ml. However, the commercial CMM kit detected 600 to $10^7$ copies/ml. It demonstrated that the primer pair of the present invention has a higher sensitivity.

Example 3

Linearity Relationship of Real-Time PCR Proceeded with the Primer Pair of the Present Invention The sequence of CMV AD 169 (NC_001347) was selected from NCBI Genebank. According to Assays by Design Service (Applied Biosystems), SEQ ID NO: 3, 5'-cctggtggactatgcttaatgct-3' and SEQ ID NO: 4, 5'-ggaagcagcaatgtcgtagtacaat-3' were designed. As to the detection of CMV AD 169, the consensus region of UL73C gene was selected as a target one which consists of 81 base pair. The probe linked label was used for detection. 6-carboxy-fluorescein (FAM) was positioned at 5' end and quencher (MGB) was located at 3' end of the probe. To carry out the reaction in one step, 3' end of the probe required phosphate functional group to prevent that the probe was regarded as primer during the reaction.

5 µl DNA sample solution was added into 10 µl 2×TaqMan Master Mix solution (ABI). 200 nM primer pair solution (SEQ ID NOs: 3 and 4), and 100 pmole probe solution (SEQ ID NO: 7, 5'-attctcatgggagcttt-3') to make 20 µl of total volume. The reaction was started with heating at 50° C. for 2 minutes. Then, 45 cycles was performed. Each cycle included denaturation (95° C. for 15 seconds) and annealing-extension (60° C. for 60 seconds).

Figure 4:
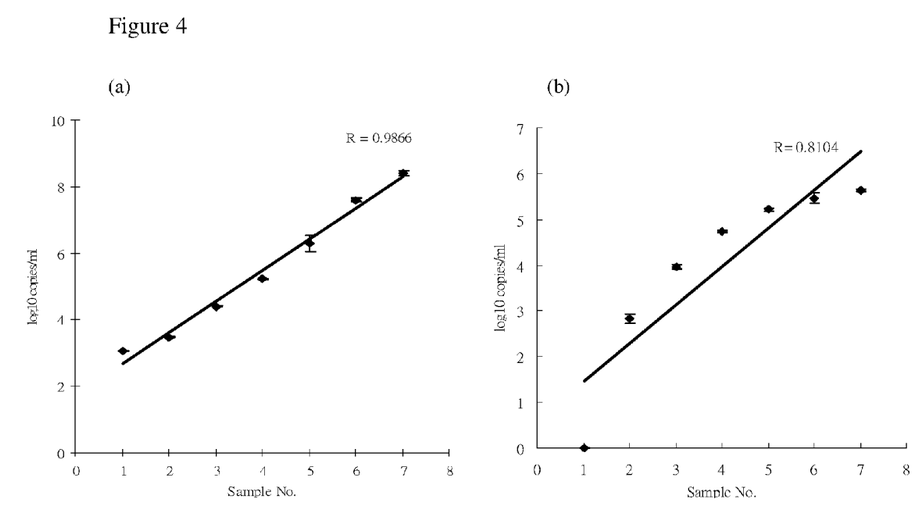

To compare with commercial CMM kit, it clearly demonstrated in FIG. 4, different DNA samples concentration by the primer pair of the present invention (SEQ ID NOs: 3 and 4) showed linearity relationship. In this example, CMV UL73 plasmid of positive control was serial diluted to make different concentration DNA samples. To compare the detection result from the commercial kit, the primer pair of the present invention (SEQ ID NOs: 3 and 4) has a higher sensitivity. The primer pair of the present invention still could detect CMV under the lower concentration of DNA samples and provided higher relationship (R=0.9866). Therefore, the primer pair of the present invention could detect the existence of CMV and reflected the real concentration of DNA samples.

Figure 5:
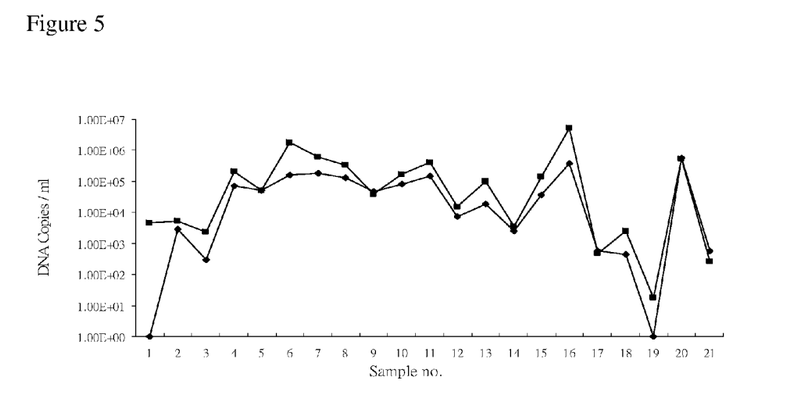
FIGS. 5 and 6 show illustration of the comparison of the sensitivity of detecting CMV between the primer pair of the present invention and the commercial kit. In the FIGS. 5 and 6, ♦ means commercial CMM kit and ■ means the kit of the present invention.
Figure 6:
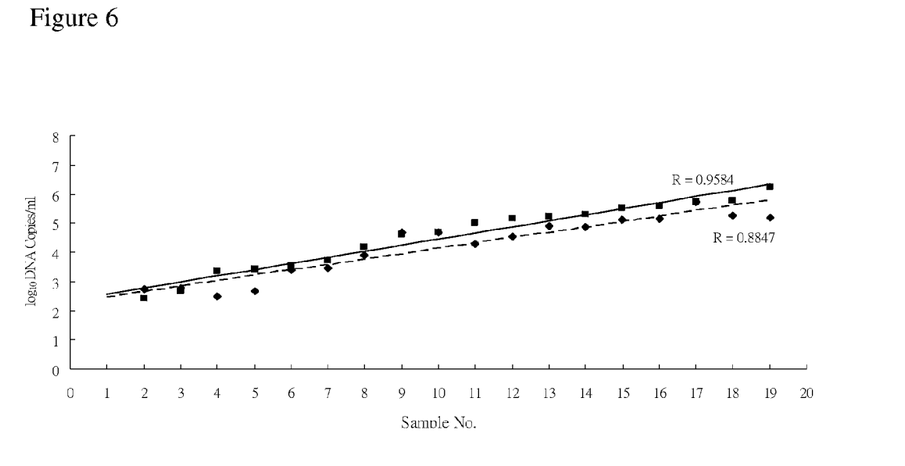

FIGS. 5 and 6 showed illustration of the comparison of the sensitivity of detecting CMV between the primer pair of the present invention and the commercial kit. 21 clinical samples were used to test. Said primer pair (SEQ ID NOs: 3 and 4) and the commercial CMM kit were proceeded with PCR. 2 samples were failed to be detected by the commercial kit, but all samples were detected by said primer pair of the present invention. In addition, the detection by said primer pair of the present invention could reflect the real change of the samples and show real DNA number thereof (FIG. 6).

Example 4

Detection of Latency or Activation of CMV

The present invention also provided a probe that traverse UL73-C1 and UL73-C2 sequences as SEQ ID NOs: 8 and 11, and got the result of real-time PCR through these probes.

The whole reaction was performed within one step method. 5 µl nucleic acid sample including clinical samples and positive control were added into 10 µl 2×TaqMan Master Mix solution (ABI), 300 nM primer pair solution (SEQ ID NO: 5, 5'-gctattgagggtggacagatttaca-3' and SEQ ID NO: 6, 5'-caggcaagccaaaccacaag-3'), and 200 nM probe solution (SEQ ID NO: 8, 5'-ctcctcctcccgccgga-3' or SEQ ID NO: 11, 5'-tctcctccctccggaac-3') to make 20 µl of total volume. The reaction was begun from reverse transcription (48° C., 30 mins). Then, 45 PCR cycles were performed. Each cycle included denaturation (95° C. for 15 seconds) and annealing-extension (60° C. for 60 seconds). Finally, PCR products were analyzed by gel electrophoresis.

Figure 7:
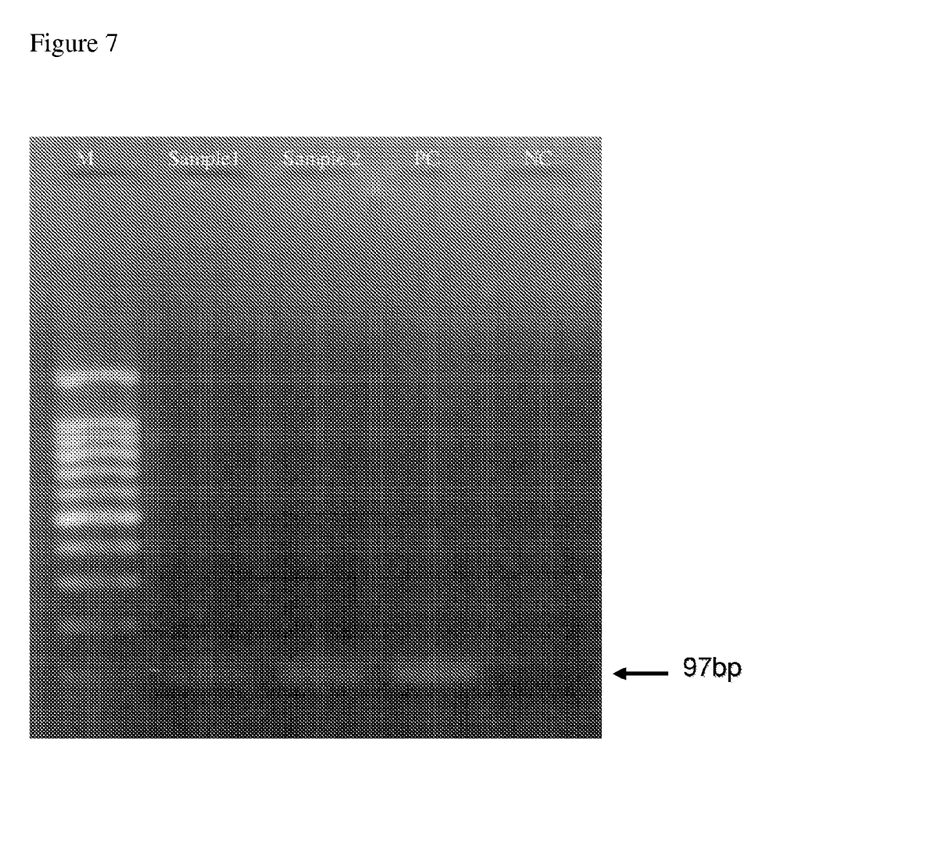
FIG. 7 shows electrophoresis illustration of the result of the primer pair of the present invention detected spliced CMV UL73/74 gene. In this figure, M means marker and PC means positive control group. NC means negative control.

As showed in FIG. 7, clinical samples (lanes 1 and 2) and positive control (lane PC) both expressed nucleic acid fragment in size about 97 bps, but not in negative control (lane NC), when primer pair (SEQ ID NOs: 5 and 6) for UL73-C1 and UL73-C2 conjunction site was proceeded with PCR. This indicated through the clinical samples that could be tested by primer pair SEQ ID NOs: 5 and 6, whether CMV was activated with spliced mRNA product. If the primer pairs SEQ ID NOs: 1 and 2 or SEQ ID NOs: 3 and 4 of the present invention could amplify corresponding UL73/74 gene fragment but primer pair SEQ ID NOs: 5 and 6 could not amplify the corresponding UL73/74 gene fragment. Such test result identified that CMV was latent inside human body and inactive.

In brief, the primer pair and probe of the present invention have higher sensitivity. These primers and probes did not only identify the infection of CMV, but also decide the level of CMV activity which inside the patients in real time. The methods and the kits provided by the present invention were superior to the traditional detecting method on understanding the real situation of infected patients.

It will be readily apparent to a person skilled in the art that varying substitutions and modification may be made to the invention disclosed herein without departing from the scope and spirit of the invention.

All patents and publications mentioned in the specification are indicative of the levels of those of ordinary skill in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations, which are not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. A method of detecting human cytomegalovirus in an individual consisting of:
   (a) isolating a nucleic acid from a sample from the individual;
   (b) providing an amplification reagent and a primer pair selected from the group consisting of an oligonucleotide consisting of,
      (i) a nucleic acid sequence consisting of at least fifteen continuous bases selected from the nucleic acid sequence of SEQ ID No: 1, SEQ ID No: 2, SEQ ID No: 3, SEQ ID No: 4, SEQ ID No: 5, SEQ ID No: 6 and SEQ ID No: 12, and
      (ii) a nucleic acid sequence fully complementary to the nucleic acid sequence of (i),
   wherein the primer pair is SEQ ID NOs: 5 and 6 or SEQ ID NOs: 12 and 6;
   (c) amplifying a target fragment corresponding to said primer pair; and
   (d) identifying the amplified fragment by gel electrophoresis followed by staining with ethidium bromide or by an oligonucleotide consisting of
      (iii) a nucleic acid sequence consisting of at least ten continuous bases selected from the nucleic acid sequence of SEQ ID No: 7, SEQ ID No: 8 and SEQ ID No: 11, and
      (iv) a nucleic acid sequence fully complementary to the nucleic acid sequence of (iii),
   wherein the oligonucleotide is used as a probe.

* * * * *

SEQUENCE LISTING

<160> NUMBER OF SEQ ID NOS: 22

<210> SEQ ID NO 1
<211> LENGTH: 27
<212> TYPE: DNA
<213> ORGANISM: artificial sequence
<220> FEATURE:
<223> OTHER INFORMATION: chemically synthesized

<400> SEQUENCE: 1
atcgcatatg tatgagctct cactgtc                                27

<210> SEQ ID NO 2
<211> LENGTH: 25
<212> TYPE: DNA
<213> ORGANISM: artificial sequence
<220> FEATURE:
<223> OTHER INFORMATION: chemically synthesized

```
<400> SEQUENCE: 2
tctggaagca gcaatgtcgt agtac                                            25

<210> SEQ ID NO 3
<211> LENGTH: 23
<212> TYPE: DNA
<213> ORGANISM: artificial sequence
<220> FEATURE:
<223> OTHER INFORMATION: chemically synthesized

<400> SEQUENCE: 3
cctggtggac tatgcttaat gct                                              23

<210> SEQ ID NO 4
<211> LENGTH: 25
<212> TYPE: DNA
<213> ORGANISM: artificial sequence
<220> FEATURE:
<223> OTHER INFORMATION: chemically synthesized

<400> SEQUENCE: 4
ggaagcagca atgtcgtagt acaat                                            25

<210> SEQ ID NO 5
<211> LENGTH: 25
<212> TYPE: DNA
<213> ORGANISM: artificial sequence
<220> FEATURE:
<223> OTHER INFORMATION: chemically synthesized

<400> SEQUENCE: 5
gctattgagg gtggacagat ttaca                                            25

<210> SEQ ID NO 6
<211> LENGTH: 20
<212> TYPE: DNA
<213> ORGANISM: artificial sequence
<220> FEATURE:
<223> OTHER INFORMATION: chemically synthesized

<400> SEQUENCE: 6
caggcaagcc aaaccacaag                                                  20

<210> SEQ ID NO 7
<211> LENGTH: 18
<212> TYPE: DNA
<213> ORGANISM: artificial sequence
<220> FEATURE:
<223> OTHER INFORMATION: chemically synthesized

<400> SEQUENCE: 7
attctcatgg gagctttt                                                    18

<210> SEQ ID NO 8
<211> LENGTH: 17
<212> TYPE: DNA
<213> ORGANISM: artificial sequence
<220> FEATURE:
<223> OTHER INFORMATION: chemically synthesized

<400> SEQUENCE: 8
ctcctcctcc cgccgga                                                     17

<210> SEQ ID NO 9
```

```
<211> LENGTH: 25
<212> TYPE: DNA
<213> ORGANISM: artificial sequence
<220> FEATURE:
<223> OTHER INFORMATION: chemically synthesized

<400> SEQUENCE: 9
cacctgtcac cgctgctata tttgc                                          25

<210> SEQ ID NO 10
<211> LENGTH: 25
<212> TYPE: DNA
<213> ORGANISM: artificial sequence
<220> FEATURE:
<223> OTHER INFORMATION: chemically synthesized

<400> SEQUENCE: 10
caccacgcag cggcccttga tgttt                                          25

<210> SEQ ID NO 11
<211> LENGTH: 17
<212> TYPE: DNA
<213> ORGANISM: artificial sequence
<220> FEATURE:
<223> OTHER INFORMATION: chemically synthesized

<400> SEQUENCE: 11
tctcctccct ccggaac                                                   17

<210> SEQ ID NO 12
<211> LENGTH: 17
<212> TYPE: DNA
<213> ORGANISM: artificial sequence
<220> FEATURE:
<223> OTHER INFORMATION: chemically synthesized

<400> SEQUENCE: 12
tgcaaccacc acgaagg                                                   17

<210> SEQ ID NO 13
<211> LENGTH: 37
<212> TYPE: DNA
<213> ORGANISM: artificial sequence
<220> FEATURE:
<223> OTHER INFORMATION: chemically synthesized; y: t or c; r: g or a

<400> SEQUENCE: 13
tgyacatcrc atatgtatga rctytcactg tccagyt                             37

<210> SEQ ID NO 14
<211> LENGTH: 28
<212> TYPE: DNA
<213> ORGANISM: artificial sequence
<220> FEATURE:
<223> OTHER INFORMATION: chemically synthesized; y: t or c; r: g or a;
      k: g or t; w: a or t

<400> SEQUENCE: 14
agttytggaa rcagcaatgt yktartwc                                       28

<210> SEQ ID NO 15
<211> LENGTH: 29
<212> TYPE: DNA
<213> ORGANISM: artificial sequence
<220> FEATURE:
<223> OTHER INFORMATION: chemically synthesized; y: t or c ; r: g or a
```

<400> SEQUENCE: 15
gcrgcytggt ggactatgct taaygctct                                29

<210> SEQ ID NO 16
<211> LENGTH: 31
<212> TYPE: DNA
<213> ORGANISM: artificial sequence
<220> FEATURE:
<223> OTHER INFORMATION: chemically synthesized; y: t or c; r: g or a;
      k: g or t

<400> SEQUENCE: 16
tggaarcagc aatgtyktar twcratacaa a                             31

<210> SEQ ID NO 17
<211> LENGTH: 35
<212> TYPE: DNA
<213> ORGANISM: artificial sequence
<220> FEATURE:
<223> OTHER INFORMATION: chemically synthesized; y: t or c; r: g or a;
      h: a, c or t; v: a, g or c

<400> SEQUENCE: 17
aaaggytatt ragggtrgah agrttyvcag cycgr                         35

<210> SEQ ID NO 18
<211> LENGTH: 35
<212> TYPE: DNA
<213> ORGANISM: artificial sequence
<220> FEATURE:
<223> OTHER INFORMATION: chemically synthesized

<400> SEQUENCE: 18
acacgcaggc aagccaaacc acaaggcaga cggac                         35

<210> SEQ ID NO 19
<211> LENGTH: 23
<212> TYPE: DNA
<213> ORGANISM: artificial sequence
<220> FEATURE:
<223> OTHER INFORMATION: chemically synthesized; s: g or c

<400> SEQUENCE: 19
attctsatgg gagcttttg tat                                       23

<210> SEQ ID NO 20
<211> LENGTH: 33
<212> TYPE: DNA
<213> ORGANISM: artificial sequence
<220> FEATURE:
<223> OTHER INFORMATION: chemically synthesized

<400> SEQUENCE: 20
ggtgcggggt ctcctcctcc cgccggaaca ccg                           33

<210> SEQ ID NO 21
<211> LENGTH: 29
<212> TYPE: DNA
<213> ORGANISM: artificial sequence
<220> FEATURE:
<223> OTHER INFORMATION: chemically synthesized

<400> SEQUENCE: 21
ggtgcgggtc tcctccckcc ggaacaccg                                29

-continued

```
<210> SEQ ID NO 22
<211> LENGTH: 30
<212> TYPE: DNA
<213> ORGANISM: artificial sequence
<220> FEATURE:
<223> OTHER INFORMATION: chemically synthesized; r: g or a; s: g or c;
      h: a, c or t

<400> SEQUENCE: 22
aactttactg craccaccac saagghtatt                                       30
```